(12) United States Patent
DeSisto

(10) Patent No.: US 7,172,592 B2
(45) Date of Patent: Feb. 6, 2007

(54) SELF-EVACUATING ELECTROCAUTERY DEVICE

(76) Inventor: Stephen R. DeSisto, 2525 Arapahoe Ave., Bldg. E-4, Unit 243, Boulder, CO (US) 80302

( * ) Notice: Subject to any disclaimer, the term of this patent is extended or adjusted under 35 U.S.C. 154(b) by 115 days.

(21) Appl. No.: 10/952,277

(22) Filed: Sep. 28, 2004

(65) Prior Publication Data

US 2005/0070891 A1 Mar. 31, 2005

Related U.S. Application Data

(60) Provisional application No. 60/506,748, filed on Sep. 29, 2003.

(51) Int. Cl.
*A61B 18/08* (2006.01)

(52) U.S. Cl. .............................. 606/49; 606/37; 606/40; 606/41

(58) Field of Classification Search .................. 606/41, 606/49, 37, 39, 40
See application file for complete search history.

(56) References Cited

U.S. PATENT DOCUMENTS

| | | | |
|---|---|---|---|
| 3,801,766 A | 4/1974 | Morrison, Jr. | |
| 4,095,071 A | 6/1978 | Chamberlain | |
| 4,347,842 A | 9/1982 | Beale | |
| 4,465,908 A | 8/1984 | Griffith et al. | |
| 4,654,488 A | 3/1987 | Westfall | |
| 4,719,914 A | 1/1988 | Johnson | |
| 5,098,430 A | 3/1992 | Fleenor | |
| 5,133,714 A | 7/1992 | Beane | |
| 5,195,959 A | 3/1993 | Smith | |
| 5,242,442 A | 9/1993 | Hirschfeld | |
| 5,244,462 A | 9/1993 | Delaheurga et al. | |
| 5,269,781 A | 12/1993 | Hewell, III | |
| 5,318,565 A | 6/1994 | Kuriloff et al. | |
| 5,360,427 A | 11/1994 | Majlessi | |
| 5,674,219 A * | 10/1997 | Monson et al. | ............... 606/45 |
| 5,800,431 A | 9/1998 | Brown | |
| 5,951,548 A * | 9/1999 | DeSisto et al. | ............... 606/42 |

OTHER PUBLICATIONS

Gatti, John E., et al. *The Mutagenicity of Electrocantery Smoke*, Plastic and Reconstructive Surgery, May 1992, pp. 781-784.
Gatti, John E., et al. *The Mutagenicity of Electrocantery Smoke, Discussion by William R. Kanter, M.D.*, Plastic and Reconstructive Surgery, May 1992, pp. 785-786.

* cited by examiner

*Primary Examiner*—S. Thomas Hughes
(74) *Attorney, Agent, or Firm*—Emery L. Tracy

(57) ABSTRACT

A device for selectively providing electrical energy from an electrosurgical generator for alternatively searing and coagulating tissue of a patient during surgery is provided. The electrocautery device has a blade electrically connected to an electrical cable. The electrocautery device comprises a hollow main body with a vacuum mechanism formed in the hollow main body. At least one intake port is formed in the hollow main body with a vacuum tubing extending into the hollow main body fluidly connecting the intake port. A first button having a first airway opening and a second airway opening selectively activates energy to sear tissue and activates the vacuum mechanism. A second button having a third airway opening selectively activates the electrical energy to coagulate tissue and activates the vacuum mechanism wherein upon depression of the first button, the first airway opening aligns with the third airway opening and wherein upon depression of the second button, the second airway opening aligns with the third airway opening.

14 Claims, 10 Drawing Sheets

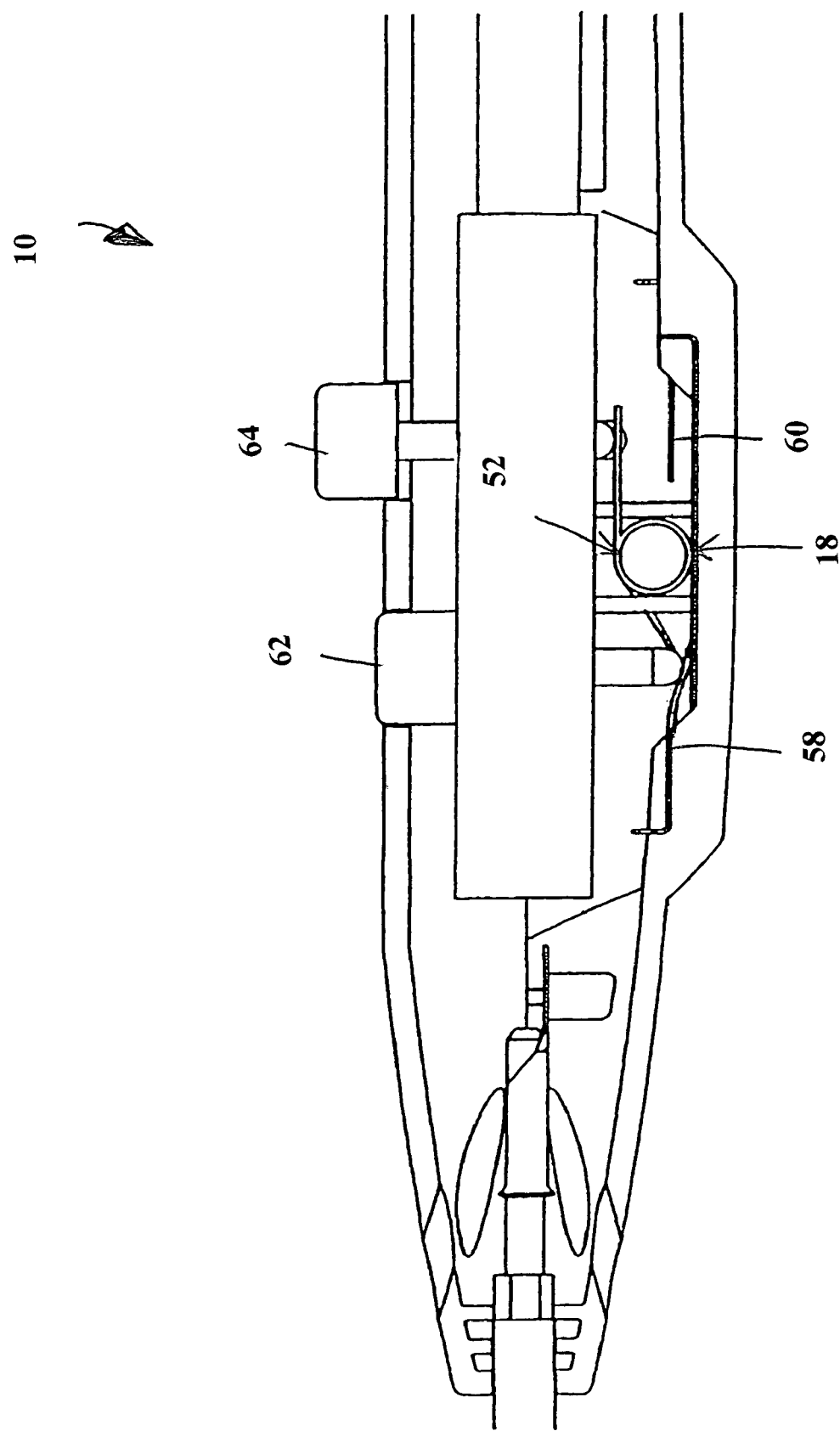

SELF-EVACUATING ELECTROCAUTERY DEVICE

The present application claim the benefit of provisional patent application Ser. No. 60/506,748, filed on Sep. 29, 2003, entitled "Self-Evacuating Electrocautery Device".

BACKGROUND OF THE INVENTION

1. Field of the Invention

This invention relates generally to electrosurgical instruments for selectively providing electrical energy from an electrosurgical generator to a patient for searing and coagulating tissue and the like and, more particularly, it relates to electrosurgical instruments for selectively providing electrical energy from an electrosurgical generator to a patient for searing and coagulating tissue and the like which further provides evacuation of the plume associated with the searing and coagulating of the tissue and the like.

2. Description of the Prior Art

With known prior art electrocautery devices, a plume, as it is referred to by persons skilled in the art is created during surgery by the vaporization of organic material (i.e., the tissue of the patient) which has been ablated by the electric current of the electrocautery device. It is widely known in the medical field that the plume created during electrosurgery is offensive and potentially dangerous to the surgeons and other operating room staff. The high temperature plume, which rises rapidly from the point of the electrosurgical instrument, has been shown to contain possible carcinogenic elements. In fact, of particular significance and concern, it has been discovered that the plume produced by electrosurgical incisions and cauterizations potentially contain and transport viable viral DNA. The viruses transmitted by the plume present a significant health hazard to the operating surgeon and others present in the operating room. In addition to the health hazards to operating personnel, sometimes the plume is produced in such volume that the surgeon's view of the operative field is obscured thereby placing the patient at substantial risk.

In the prior art, systems have been developed for aspirating the plume produced by electrocautery devices in electrosurgical procedures. In the typical technique, a conventional hospital suction tube held near the site of electrosurgical procedure by an assistant aspirates the plume. Unfortunately, this method inefficiently requires the fulltime attention of the assistant and the placement of the often bulky suction tube in the operative field which obstructs the operating surgeon's view. Additionally, since conventional suction tubes that are attached to a vacuum system create substantial noise levels in the operating room coupled with the fact that the suction tubes operate on a continuous basis during surgery, the suction tubes interfere with normal operating room dialogue thereby potentially causing miscommunications and misunderstandings between the operating room surgeon and the operating room staff.

SUMMARY

The present invention is an electrocautery device for selectively providing electrical energy from an electrosurgical generator for alternatively searing and coagulating tissue of a patient during surgery. The electrocautery device has a blade and an electrical cable with the cable electrically connecting the blade to the electrosurgical generator. The electrocautery device comprises a hollow main body with the hollow main body having a first aperture and a second aperture. Vacuum means are formed in the hollow main body for selectively providing a vacuum for removing any plume created while searing or coagulating tissue with the blade of the electrocautery device. At least one intake port is formed in the hollow main body. A vacuum tubing extends into the hollow main body and fluidly connected to the intake port. A first button is positioned within the first aperture of the hollow main body to selectively activate the electrical energy of the electrosurgical generator to sear tissue and to activate the vacuum means upon activation of the electrical energy with the first button having a first airway opening and a second airway opening. A second button is positioned within the second aperture of the hollow main body to selectively activate the electrical energy of the electrosurgical generator to coagulate tissue and to activate the vacuum means upon activation of the electrical energy with the second button having a third airway opening wherein upon depression of the first button, the first airway opening aligns with the third airway opening to connect the intake port to the vacuum tubing upon activation of both the electrical energy and the vacuum means and wherein upon depression of the second button, the second airway opening aligns with the third airway opening to connect the intake port to the vacuum tubing upon activation of both the electrical energy and the vacuum means.

In addition, the present invention includes an electrosurgical instrument for selectively providing electrical energy from an electrosurgical generator to a patient for searing and coagulation with the electrosurgical instrument having an electrode blade electrically connected to the electrosurgical generator. The instrument comprises a hollow elongated body and a blade receiving opening in the hollow elongated body for receiving the electrode blade. At least one plume intake port is formed in the elongated body adjacent the electrode blade. Push button activation means are mounted within the hollow elongated body for selectively searing or coagulating. Airway means are formed in the push button activation means for fluidly connecting each intake port to a vacuum mechanism.

The present invention further includes a method for selectively providing electrical energy from an electrosurgical generator for alternatively searing and coagulating tissue of a patient during surgery. The method comprises providing a hollow main body, connecting a vacuum mechanism to the hollow main body, forming at least one intake port in the hollow main body, positioning an automatically returning first button in the hollow main body, positioning an automatically returning second button in the hollow main body, depressing the first button for selectively activating the electrical energy of the electrosurgical generator to sear tissue and to activate the vacuum mechanism upon activation of the electrical energy or depressing the second button for selectively activating the electrical energy of the electrosurgical generator to coagulate tissue and to activate the vacuum means upon activation of the electrical energy, and opening airways in the first button and second button alignable within the hollow main body to connect each intake port to the vacuum mechanism upon activation of both the electrical energy and the vacuum mechanism.

BRIEF DESCRIPTION OF THE DRAWINGS

FIG. 10 is a sectional view of the self-evacuating electrocautery device of FIG. 1, constructed in accordance with the present invention, with the front button depressed.

DETAILED DESCRIPTION OF THE PREFERRED EMBODIMENTS

Figure 1:
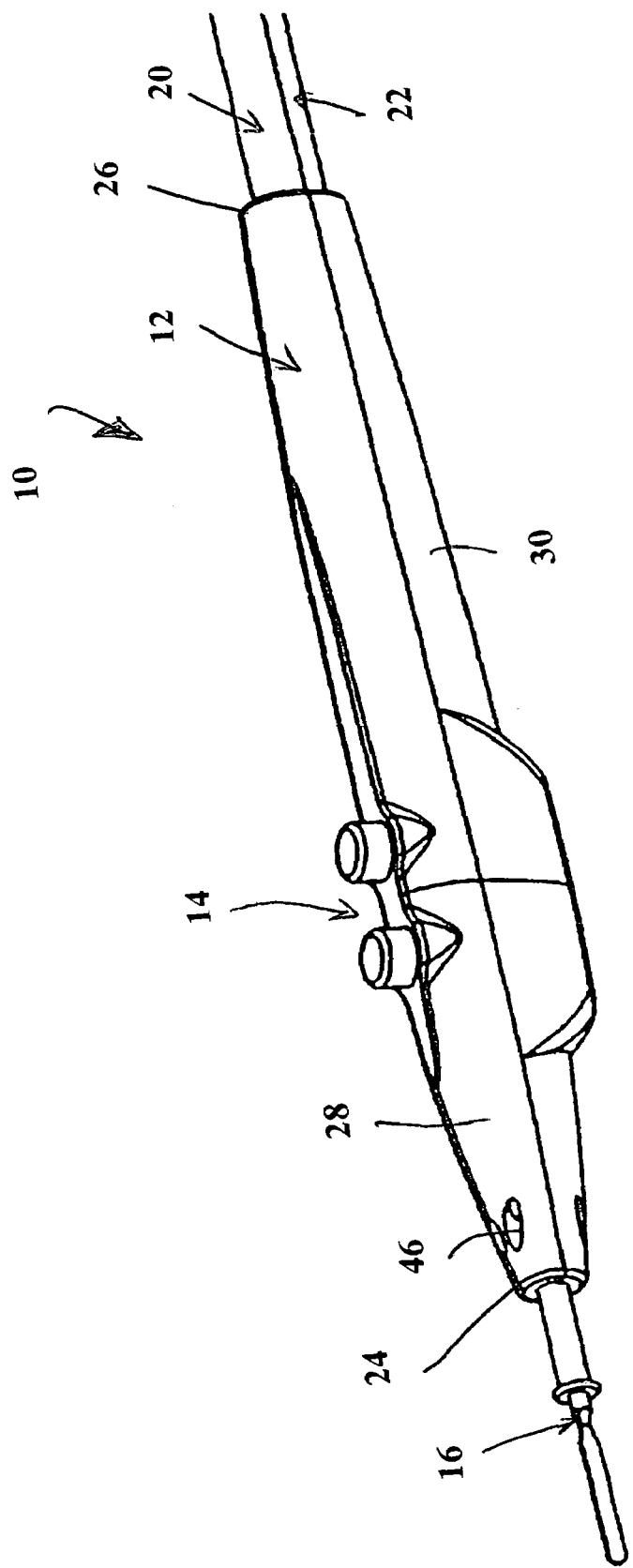
FIG. 1 is a perspective view illustrating the self-evacuating electrocautery device, constructed in accordance with the present invention.
Figure 2:
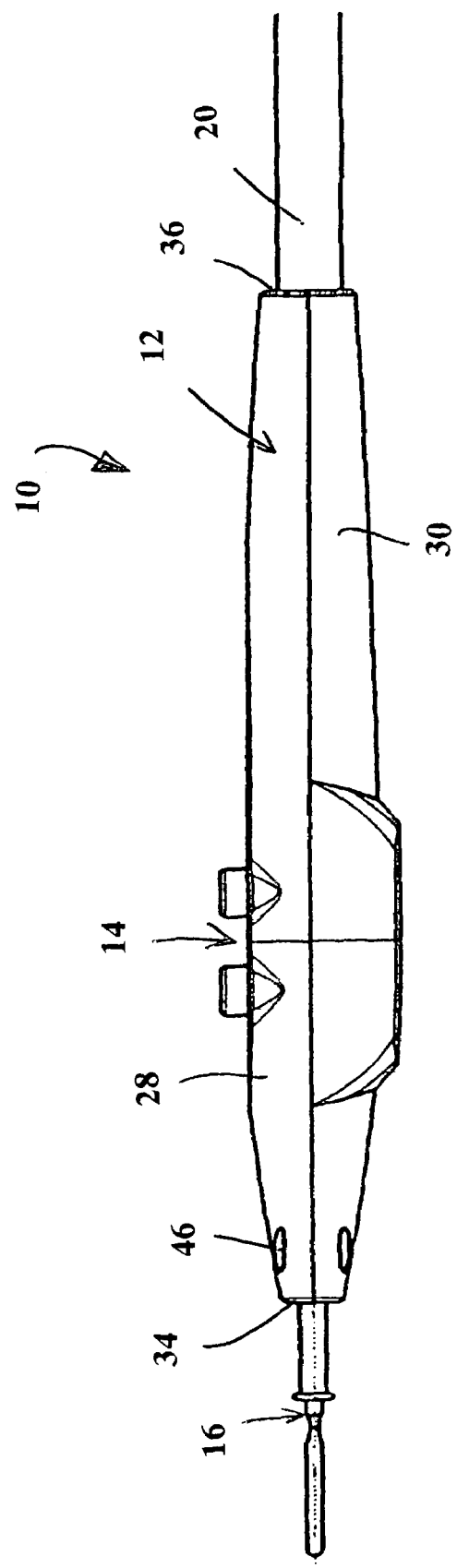
FIG. 2 is an elevational side view illustrating the self-evacuating electrocautery device of FIG. 1, constructed according to the present invention.
Figure 3:
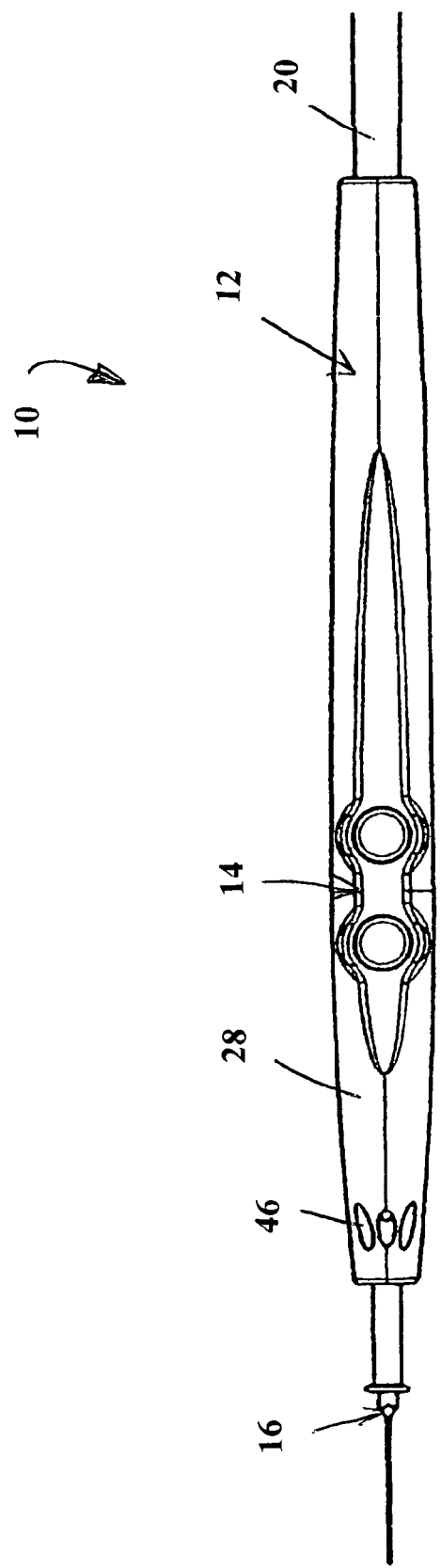
FIG. 3 is a top view illustrating the self-evacuating electrocautery device of FIG. 1, constructed in accordance with the present invention.
Figure 4:
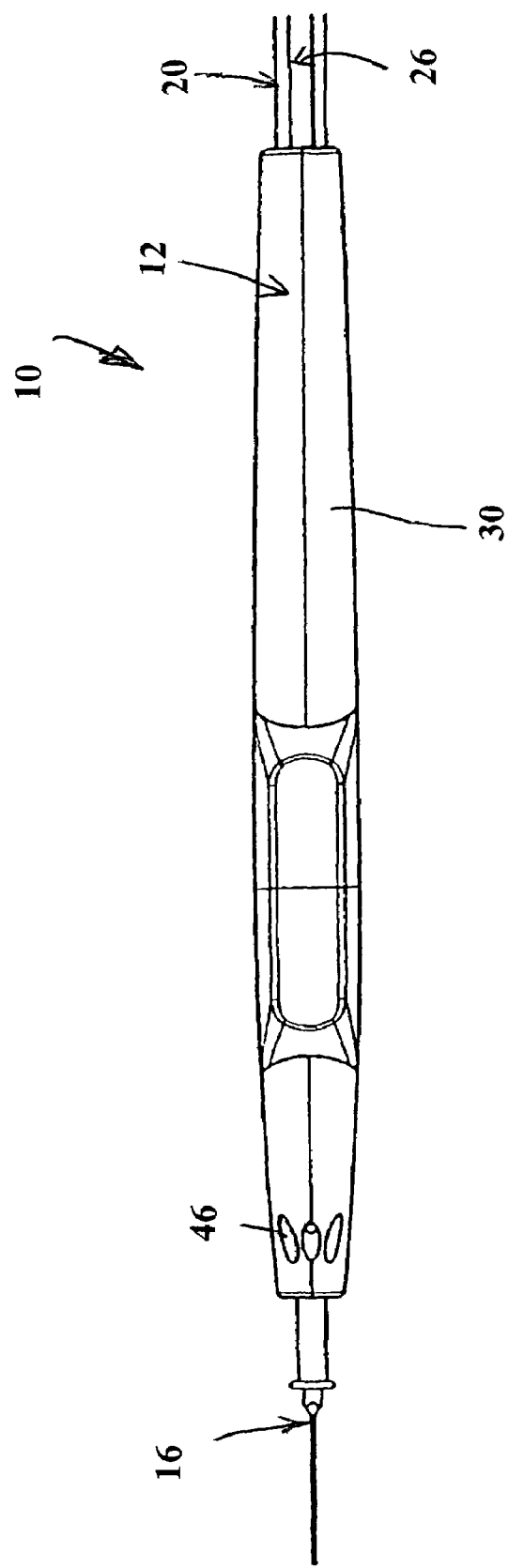
FIG. 4 is a bottom view illustrating the self-evacuating electrocautery device of FIG. 1, constructed in accordance with the present invention.
Figure 5:
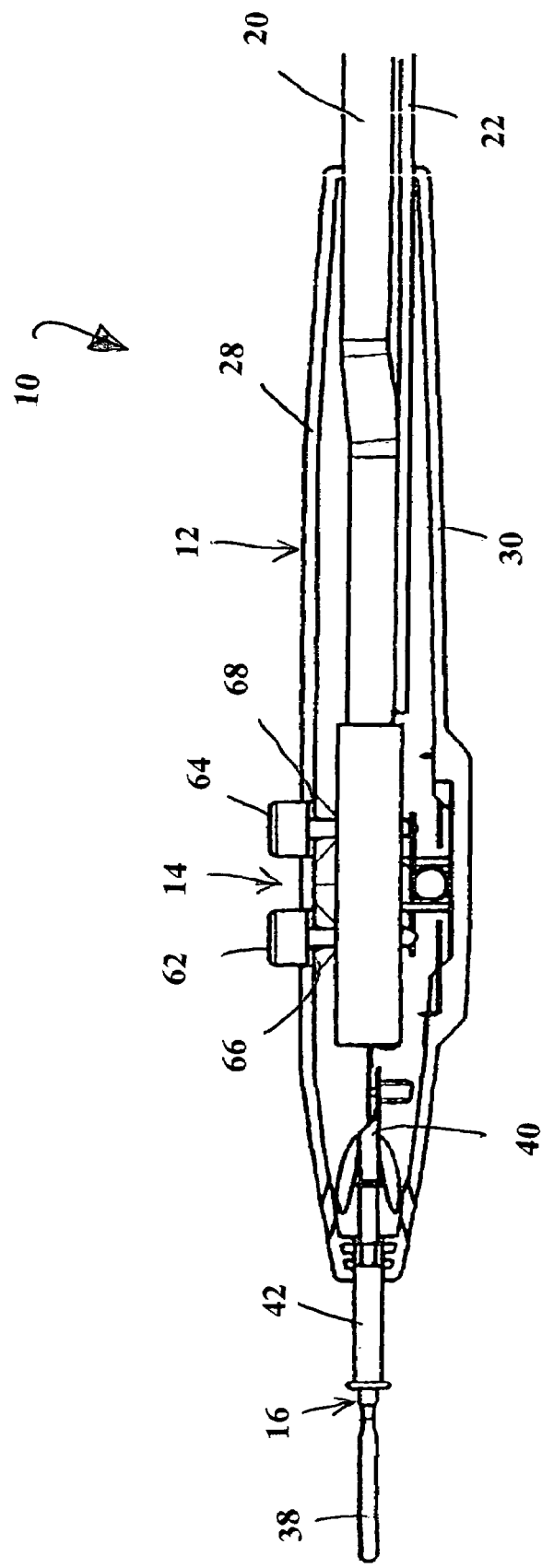
FIG. 5 is a sectional view illustrating a the self-evacuating electrocautery device of FIG. 1, constructed in accordance with the present invention.
Figure 6:
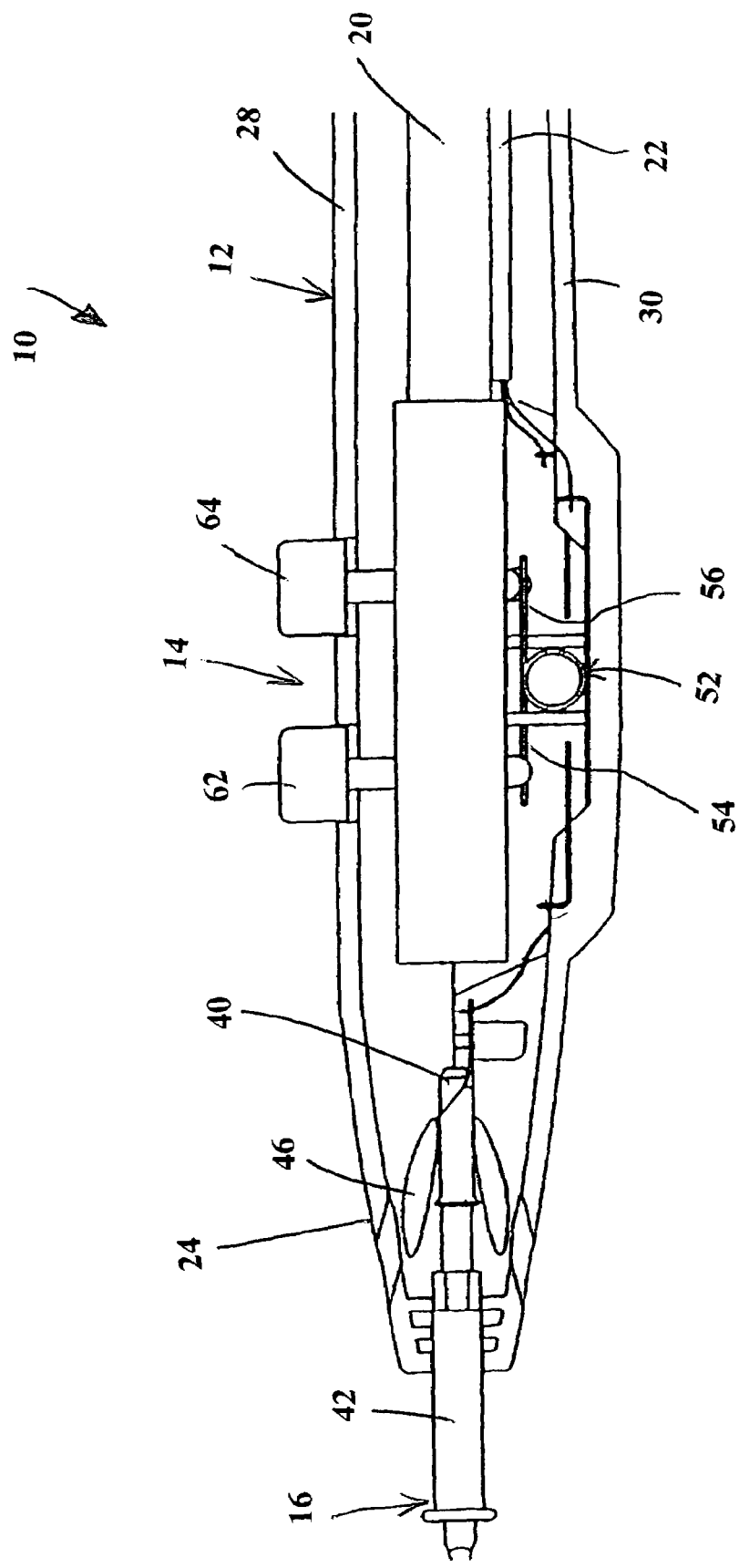
FIG. 6 is another sectional view illustrating the self-evacuating electrocautery device of FIG. 1, constructed in accordance with the present invention.
Figure 7:
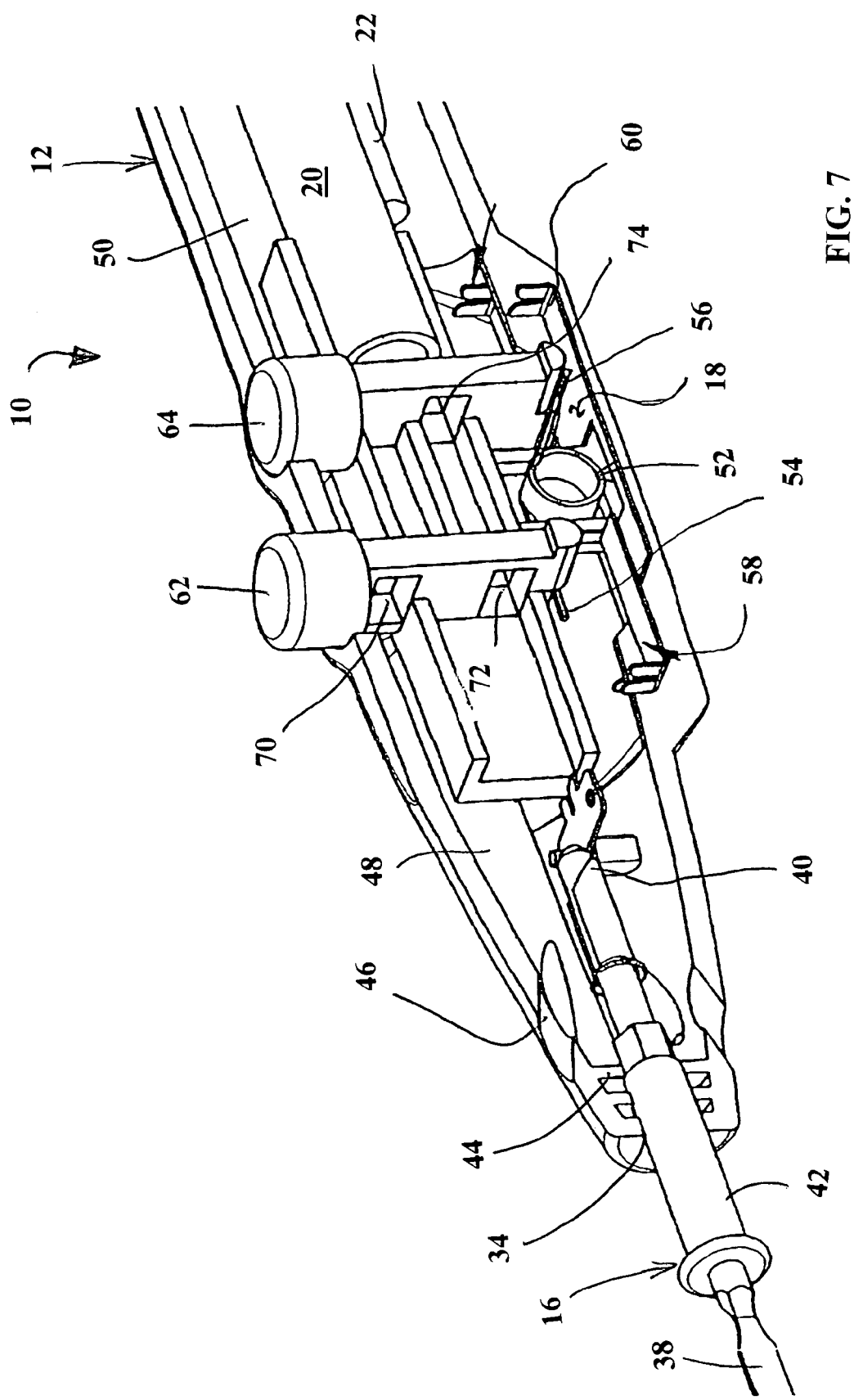
FIG. 7 is a sectional perspective view illustrating the self-evacuating electrocautery device of FIG. 1, constructed in accordance with the present invention, with the rear button depressed opening the bottom airway channel.
Figure 8:
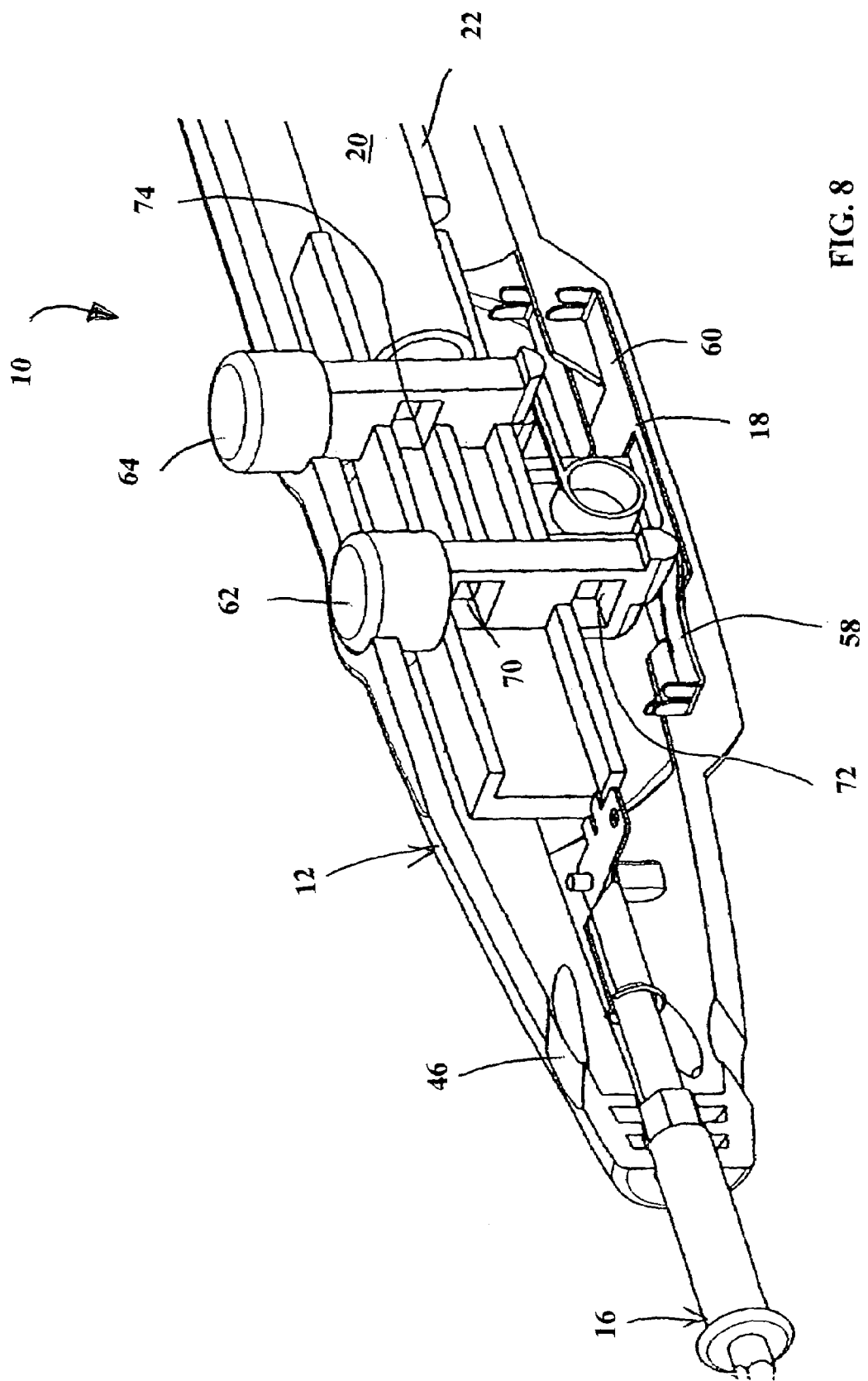
FIG. 8 is a sectional perspective view illustrating the self-evacuating electrocautery device of FIG. 1, constructed in accordance with the present invention, with the front button depressed opening the top airway channel.
Figure 9:
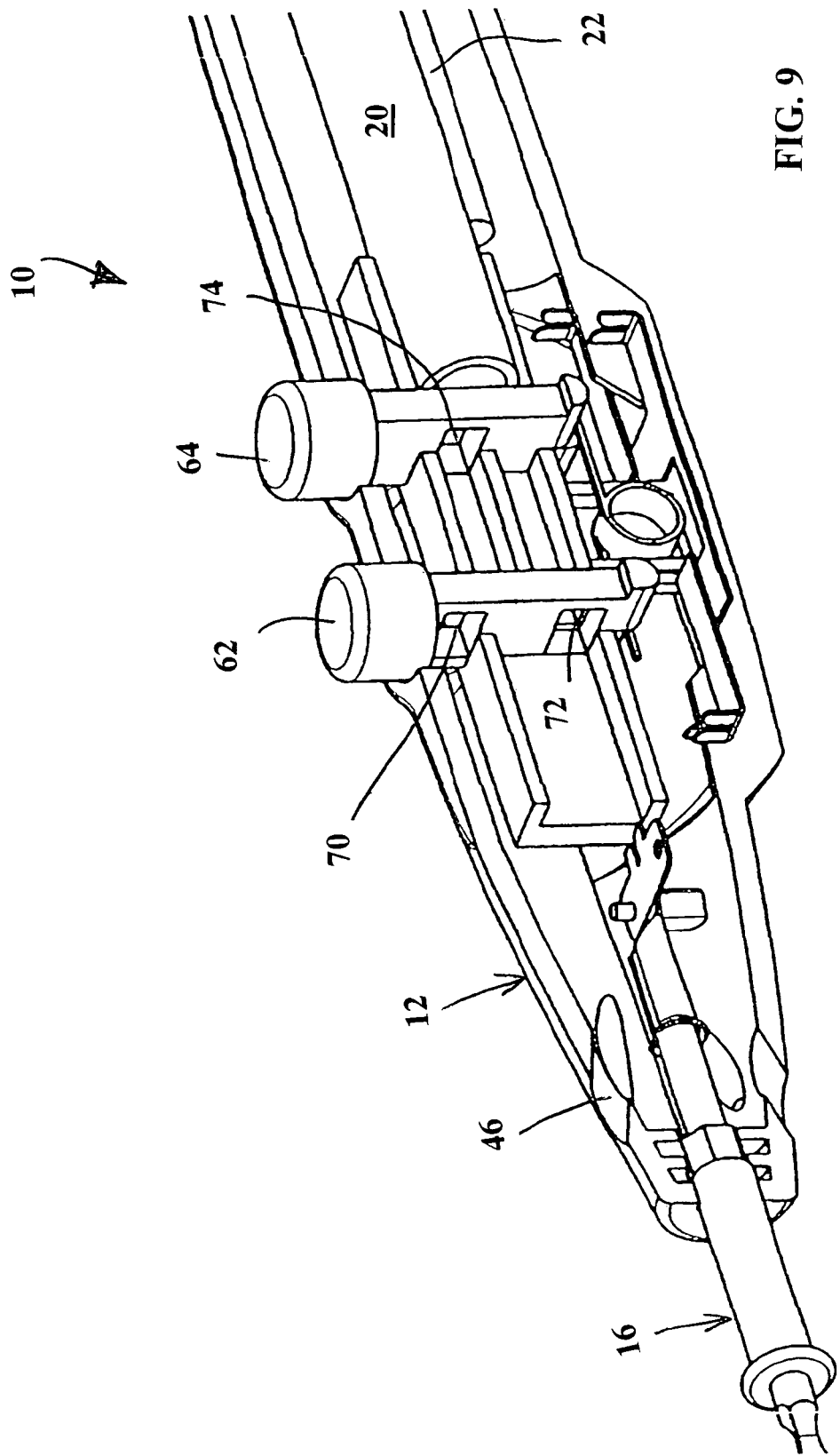
FIG. 9 is a sectional perspective view illustrating the self-evacuating electrocautery device of FIG. 1, constructed in accordance with the present invention, with no buttons depressed maintaining closure of the top and bottom airway channels.

As illustrated in FIGS. 1–10, the present invention is a disposable self-evacuating electrocautery device, indicated generally at 10, for removing plume created by searing and coagulating tissue and the like during surgical operations with the electrocautery device 10. Typically, the electrocautery device 10 of the present invention comprises an elongated hollow body 12, a push button activation mechanism 14, a disposable electrocautery blade 16, an electrical contact member 18, flexible plume vacuum tubing 20 connected to a vacuum system (not shown) and an insulated electrical cable 22 electrically connected to a conventional electrosurgical generator (not shown). While the electrocautery device 10 is preferably prepackaged in sterilized containers to be used once and then disposed, it is within the scope of the present invention to have the electrocautery device 10 be non-disposable and disinfectable for re-use by known procedures in the art.

The hollow body 12 of the electrocautery device 10 has a first end 24 and a second end 26 and comprises a first body portion 28 and a second body portion 30. The first body portion 28 includes a first push button aperture 66 and a second push button aperture 68 for receiving the push button activation mechanism 14. Preferably, the first body portion 28 is fixably secured to the second body portion 30 by ultrasonic welding or other means including, but not limited to, adhesive, mechanical means, etc.

The first body and second body portions 28, 30 of the hollow body 12 can, but not necessarily, further include a plurality of first spaced ribs 44 integrally adjacent the first end 24 of the hollow body 12 and a plurality of second spaced ribs (not shown) along and integrally adjacent the second end 26 of the hollow body 12 on both the first body portion 28 and the second body portion 30. The first and second ribs are preferably formed integral to the first and second body portions 28, 30, respectively, from the same materials used to form the hollow body 12 during construction of the hollow body 12. While described as being integral to the first and second body portions 28, 30, it is within the scope of the present invention, however, to construct the first and second ribs from a different material than the material used for the hollow body 12 and, also, to add the first and second ribs to the first and second body portions 28, 30, respectively, after the hollow body 12 has been constructed.

The hollow body 12, in a preferred embodiment of the electrocautery device 10 of the present invention, is constructed from an inexpensive, thermoplastic, electrically non-conductive material. It is within the scope of the present invention, however, to construct the hollow body 12 from other materials including, but not limited to, ceramic, wood, other plastics, etc.

The hollow body 12 of the electrocautery device 10 additionally comprises a first opening 34 formed in the first end 24 of the hollow body 12 for receiving the blade 16 and a second opening 36 formed in the second end 26 of the hollow body 12 opposite the first opening 34 for receiving the cable 22 and the plume vacuum tubing 20. The blade 16 of the electrocautery device 10 comprises a blade portion 38 for use in alternatively searing or coagulating tissue and the like during surgery, a contact end 40 opposite the blade portion 38 for contacting the electrical contact member 18, and an insulating sheath 42 positioned about the blade 16 substantially between the blade portion 38 and the contact portion 40. The blade 16 is positioned such that the insulating sheath 42 of the blade 16 is seated and secured within the first end 24 of the hollow body 12 between the first body portion 28 and the second body portion 30 with the blade portion 38 extending away from the hollow body 12. The first spaced ribs 44 of the hollow body 12 inhibit lateral and transverse movement of the blade 16 within the hollow body 12.

The hollow body 12 can also, but not necessarily, comprise a plurality of plume intake ports 46 feeding into the first end 24 of the hollow body 12 and defined by the first and second body portions 28, 30 of the hollow body 12. The plume intake ports 46 are positioned about the first end 24 of the hollow body 12 in close proximity to the blade 16 effectively remove the plume created during surgical operations. The plume intake ports 46 can be arranged in a circumferential configuration about the first end 24 of the hollow body 12. Function and operation of the plume intake ports 46 in conjunction with first and second airway paths 48, 50 and the plume vacuum tubing 20 will be described in further detail below.

In another embodiment of the electrocautery device 10, the plume intake ports 46 are replaced by apertures (not shown) formed around the insulating sheath 42 of the blade portion 38. These apertures operate and function similar to the plume intake ports 46 described above.

The electrical cable 22 of the electrocautery device 10 is positioned within the second airway path 50 in the second end 26 of the hollow body 12 and extends rearwardly away from the hollow body 12 through the second opening 36 in the second end 26 of the hollow body 12 to an electrosurgical generator. As mentioned briefly above, the electrocautery device 10 of the present invention comprises a main conducting contact member 18 having a first end 58 and a second end 60 with the second end being connected to the electrical cable 22. A searing/coagulating conducting member 52 having a searing portion 54 and a coagulating portion 56 is mounted adjacently above the main contact member 18 and alternatively selectively contactable with the main contact member 18. The searing portion 54 and the coagulating portion 56 are alternatively movable into contact with the first end 58 and the second end 60 of the main contact member 18, respectively, and serve as electrical contacts for the activation mechanism 14 upon depression of the activation mechanism 14 into searing and coagulating positions, respectively, to sear and coagulate tissue as desired.

The electrical contact member 18 is preferably formed from a single metal stamping. It should be noted, however, that construction of the contact member 18 by other means, besides metal stamping, is within the scope of the present invention.

The activation mechanism 14 of the electrocautery device 10 of the present invention, includes a depressable searing button 62 and a depressable coagulating button 64 positioned within the first button aperture 66 and the second button aperture 68, respectively, of the hollow body 12 and contactable with the searing portion 54 and the coagulating portion 56, respectively, of the searing/coagulating conducting member 52.

The searing button 62 and the coagulating button 64, when not in use, returns to its original position via the spring-like searing/coagulating conducting member 52 into a neutral, non-electrical contact position. On the other hand, the activation mechanism 14, in operation, is intermittently movable into either a searing position or a coagulating position and controls the electrical current delivered to the blade 16 while correspondingly activating the vacuum system and the self-evacuating features of the electrocautery device 10 of the present invention. Both the electrical control by the activation mechanism 14 and the self-evacuating features of the electrocautery device 10 of the present invention will be discussed in more detail below.

The searing button 62 of the activation mechanism 14 of the electrocautery device 10 of the present invention includes a first airway opening 70 and a second airway opening 72 and the coagulating button 64 of the activation mechanism 14 includes a third airway opening 74. In the non-activated position, none of the airways are aligned. In the searing position with the searing button 62 depressed, the first airway opening 70 of the searing button 62 aligns with the third airway opening 74 of the coagulating button 64 thereby opening the first and second airway paths 48, 50 from the plume intake ports 46 to the plume vacuum tubing 20. In the coagulating position with the coagulating button 64 depressed, the second airway opening 72 of the searing button 62 aligns with the third airway opening 74 of the coagulating button 64 thereby opening the first and second airway paths 48, 50 from the plume intake ports 46 to the plume vacuum tubing 20.

The procedure of using the electrocautery device 10 of the present invention will now be described. In use, a surgeon or other medical professional grasps the electrocautery device 10 and positions the electrocautery device 10 adjacent the desired tissue to be seared or coagulated. To sear the desired tissue, the surgeon or other medical professional activates the electrocautery device 10 into the searing position by depressing the searing button 62 of the activation mechanism 14. The depression of the searing button 62 causes the searing portion 54 of the searing/coagulating conducting member 52 to move into contact with the first end 58 of the main contact member 18. The contact between the searing portion 54 of the searing/coagulating conducting member 52 and the first end 58 of the main contact member 18 connects the circuit between the searing/coagulating conducting member 52 and the main contact member 18 to provide both electrical energy to the blade 16 to sear the desired tissue and electrical energy to the vacuum to evacuate the plume associated with the searing of the desired tissue.

When the searing button 62 of the activation mechanism 14 causes the searing portion 54 of the searing/coagulating conducting member 52 to contact the first end 58 of the main contact member 18, the first airway opening 70 of the searing button 62 aligns with the third airway opening 74 in the coagulating button 64 fluidly connecting the first and second airway paths 48, 50 in the hollow body 12 thereby connecting the plume intake ports 46 with the vacuum tubing 20 and, thus, the waste receptacle. When the desired searing is completed, the surgeon or other medical professional releases the pressure on the searing button 62 of the activation mechanism 14 causing the searing button 62 to automatically return back to the neutral position moving the searing portion 54 of the searing/coagulating conducting member 52 out of contact with the first end 58 of the main contact member 18 thereby disconnecting the connection and circuit between the searing/coagulating conducting member 52 and the main contact member 18 ceasing electrical current to both the blade 16 and the vacuum.

Coagulation of tissue utilizing the electrocautery device 10 of the present invention is similar to the procedures for searing tissue. To coagulate tissue and the like, the surgeon or other medical professional activates the electrocautery device 10 into the coagulating position by depressing the coagulating button 64 of the activation mechanism 14. The depression of the coagulating button 64 causes the coagulating portion 56 of the searing/coagulating conducting member 52 to move into contact with the second end 60 of the main contact member 18. The contact between the coagulating portion 56 of the searing/coagulating conducting member 52 and the second end 60 of the main contact member 18 connects the circuit between the searing/coagulating contacting member 52 and the main contact member 18 to provide electrical current to the blade 16 to coagulate the desired tissue and activate the vacuum on the waste receptacle.

When the coagulating button 64 of the activation mechanism 14 causes the coagulating portion 56 of the searing/coagulating conducting member 52 to contact the first end 58 of the main contact member 18, the second airway opening 72 of the searing button 62 aligns with the third airway opening 74 of the coagulating button 56 connecting the first and second airway paths 48, 50 in the hollow body 12 thereby connecting the plume intake ports 46 with the vacuum tubing 20 and, thus, the waste receptacle. When the desired coagulating is completed, the surgeon or other medical professional releases the pressure on the coagulating button 64 of the activation mechanism 14 causing the coagulating button 64 to automatically return back to the neutral position moving the coagulating portion 56 of the searing/coagulating contacting member 52 out of contact with the second end 60 of the main contact member 18 thereby disconnecting the connection and circuit between the searing/coagulating contacting member 52 and the main contact member 18 ceasing electrical current to both the blade 16 and the vacuum.

It thus follows that when the electrocautery device 10 of the present invention is in use, being connected to both the electrosurgical generator and the vacuum source, the mutagenic plume created by contact of the blade 16 with the tissue will be immediately evacuated from the operating site to the vacuum source. Of course, suitable filtering systems may be associated with the vacuum system to dispose of contaminants in the materials being drawn to the vacuum source.

In sum, the present invention is a self-evacuating electrocautery device 10 for providing electrical energy from an electrosurgical generator for alternately searing and coagulating tissue while simultaneously evacuating the generated smoke plume during surgery. The electrocautery device 10 has a blade 16, integral switching and valve assembly 14, an electrical cable 22 for electrically connecting the blade 16 to the electrosurgical generator, and vacuum tubing 20 to provide smoke plume evacuation from a remote vacuum source.

The electrocautery device 10 comprises an elongated hollow body 12 having a first opening 24, a second opening 26, a first button aperture 66, a second button aperture 68, and at least one intake port 46. The first opening 24 receives the blade 16, the second opening receives the electrical cable 22 and vacuum tubing 20, the first button aperture 66 receives the searing button 62, the second button aperture 68 receives the coagulating button 64, and the intake ports 46 are adjacent the blade for receiving any smoke plume.

Vacuum means are formed as an encased push button valve assembly 14 situated within the elongated hollow body 12 with integral electrical contacts 18; an alternating pair of dual function buttons 62, 64 for selectively allowing vacuum for removing any plume created while searing or coagulating tissue with the blade 16 of the electrocautery device 10; wherein the vacuum means comprises at least one intake port 46 formed adjacent the first opening 34 of the hollow body 12, a vacuum tubing 20 extending through the second opening 36 of the hollow body 12 and connected to the button valve assembly 14.

A push button mechanism 14 is integrally enclosed within the hollow body 12 for selectively controlling the electrical energy to the blade 16, the switch means 14 having a combination of contacts 52 activated by the alternate depression of the auto-returning buttons 62, 64 to selectively activate the electrical energy of the electrosurgical generator to either sear or coagulate tissue and to activate the vacuum means upon activation of the electrical energy and further comprises path means 70, 72, 74 formed in the buttons 62, 64 for selectively connecting the intake port 46 to the vacuum tubing 20 upon activation of both the electrical energy, the path means 70, 72, 74 having airway paths alternatingly alignable within the switch/valve body to connect the intake port 46 to the vacuum tubing 20 upon activation of both the electrical energy and the vacuum means.

The foregoing exemplary descriptions and the illustrative preferred embodiments of the present invention have been explained in the drawings and described in detail, with varying modifications and alternative embodiments being taught. While the invention has been so shown, described and illustrated, it should be understood by those skilled in the art that equivalent changes in form and detail may be made therein without departing from the true spirit and scope of the invention, and that the scope of the present invention is to be limited only to the claims except as precluded by the prior art. Moreover, the invention as disclosed herein, may be suitably practiced in the absence of the specific elements which are disclosed herein.

What is claimed is:

1. An electrocautery device for selectively providing electrical energy from an electrosurgical generator for alternatively searing and coagulating tissue of a patient during surgery, the electrocautery device having a blade and an electrical cable, the cable electrically connecting the blade to the electrosurgical generator, the electrocautery device comprising:

a hollow main body, the hollow main body having a first aperture and a second aperture;

vacuum means formed in the hollow main body for selectively providing a vacuum for removing any plume created while searing or coagulating tissue with the blade of the electrocautery device;

at least one intake port formed in the hollow main body;

a vacuum tubing extending into the hollow main body and fluidly connected to the intake port;

a first button positioned within the first aperture of the hollow main body to selectively activate the electrical energy of the electrosurgical generator to sear tissue and to activate the vacuum means upon activation of the electrical energy, the first button having a first airway opening and a second airway opening; and a second button positioned within the second aperture of the hollow main body to selectively activate the electrical energy of the electrosurgical generator to coagulate tissue and to activate the vacuum means upon activation of the electrical energy, the second button having a third airway opening;

wherein upon depression of the first button, the first airway opening aligns with the third airway opening to connect the intake port to the vacuum tubing upon activation of both the electrical energy and the vacuum means; and wherein upon depression of the second button, the second airway opening aligns with the third airway opening to connect the intake port to the vacuum tubing upon activation of both the electrical energy and the vacuum means.

2. The electrocautery device of claim 1 and further comprising:

an electrical contact within the hollow main body, the electrical contact electrically connecting the blade and the electric cable to selectively control the electrical charge to the blade to either sear or coagulate tissue and to activate the vacuum means.

3. The electrocautery device of claim 2 and further comprising:

a searing/coagulating conducting member adjacent the electrical contact, the searing/coagulating conducting member having a searing portion and a coagulating portion, the searing portion contacting the electrical contact upon depression of the first button, the coagulating portion contacting the electrical contact upon depression of the second button.

4. The electrocautery device of claim 3 wherein the searing/coagulating conducting member functions as a spring to return the first button and the second button to a deactivated position.

5. The electrocautery device of claim 1 wherein the hollow main body comprises an elongated hollow body having a longitudinal length, a first opening and a second opening, the first opening receiving the blade and the second opening receiving the electrical cable and vacuum tubing.

6. The electrocautery device of claim 1 wherein the hollow main body includes a plurality of ribs to inhibit movement of the blade and electrical cable, respectively, within the hollow body.

7. An electrosurgical instrument for selectively providing electrical energy from an electrosurgical generator to a patient for searing and coagulation, the electrosurgical instrument having an electrode blade electrically connected to the electrosurgical generator, the instrument comprising:
- a hollow elongated body;
- a blade receiving opening in the hollow elongated body for receiving the electrode blade;
- at least one plume intake port formed in the elongated body adjacent the electrode blade;
- push button activation means mounted within the hollow elongated body for selectively searing or coagulating; and
- airway means formed in the push button activation means for fluidly connecting each intake port to a vacuum mechanism;
- wherein the push button activation means includes a first button for selectively activating the electrical energy of the electrosurgical generator to sear tissue and to activate the vacuum means upon activation of the electrical energy, the first button having a first airway opening and a second airway opening;
- wherein the push button activation means includes a second button for selectively activating the electrical energy of the electrosurgical generator to coagulate tissue and to activate the vacuum means upon activation of the electrical energy, the second button having a third airway opening; and
- wherein the airway means includes a first airway opening and a second airway opening in the first button and a third airway opening in the second button wherein upon depression of the first button, the first airway button aligns with the third airway opening to connect the intake port to the vacuum mechanism upon activation of both the electrical energy and the vacuum mechanism and wherein upon depression of the second button, the second airway opening aligns with the third airway opening to connect the intake port to the vacuum mechanism upon activation of both the electrical energy and the vacuum mechanism.

8. The electrosurgical instrument of claim 7 and further comprising:
- an electrical contact within the hollow main body, the electrical contact electrically connecting the blade and the electric cable to selectively control the electrical charge to the blade to either sear or coagulate tissue and to activate the vacuum mechanism.

9. The electrosurgical instrument of claim 8 and further comprising:
- a searing/coagulating conducting member adjacent the electrical contact, the searing/coagulating conducting member having a searing portion and a coagulating portion, the searing portion contacting the electrical contact upon depression of the first button, the coagulating portion contacting the electrical contact upon depression of the second button.

10. The electrosurgical instrument of claim 9 wherein the searing/coagulating conducting member functions as a spring to return the first button and the second button to a deactivated position.

11. The electrosurgical instrument of claim 7 wherein the hollow main body comprises an elongated hollow body having a longitudinal length, a first opening and a second opening, the first opening receiving the blade and the second opening receiving the electrical cable and the vacuum tubing.

12. A method for selectively providing electrical energy from an electrosurgical generator for alternatively searing and coagulating tissue of a patient during surgery, the method comprising:
- providing a hollow main body;
- connecting a vacuum mechanism to the hollow main body;
- forming at least one intake port in the hollow main body;
- positioning an automatically returning first button in the hollow main body, the first button having a first airway opening and a second airway opening;
- positioning an automatically returning second button in the hollow main body, the second button having a third airway opening;
- depressing the first button;
- selectively activating the electrical energy of the electrosurgical generator to sear tissue and to activate the vacuum mechanism upon activation of the electrical energy or depressing the second button for selectively activating the electrical energy of the electrosurgical generator to coagulate tissue and to activate the vacuum means upon activation of the electrical energy;
- aligning the first airway opening and the third airway to connect each intake port to the vacuum mechanism upon activation of both the electrical energy and the vacuum mechanism; and
- opening airways in the first button and second button alignable within the hollow main body to connect each intake port to the vacuum mechanism upon activation of both the electrical energy and the vacuum mechanism.

13. The method of claim 12 wherein the first button includes a first airway opening and a second airway opening and the second button includes a third airway opening and further comprising:
- aligning the second airway opening and the third airway opening to connect each intake port to the vacuum mechanism upon activation of both the electrical energy and the vacuum mechanism.

14. The method of claim 12 and further comprising:
- mounting an electrical contact within the hollow main body, the electrical contact electrically connecting the blade and the electric cable to selectively control the electrical charge to the blade to either sear or coagulate tissue and to activate the vacuum mechanism.

* * * * *